US012690851B2

(12) United States Patent
Birk et al.

(10) Patent No.: US 12,690,851 B2
(45) Date of Patent: Jul. 28, 2026

(54) ADAPTOR FOR SURGICAL RETRACTORS

(71) Applicant: The Research Foundation for the State University of New York, Albany, NY (US)

(72) Inventors: Daniel Birk, Setauket, NY (US); Vincent DeStefano, East Setauket, NY (US); Nicole Hershkowitz, East Setauket, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 243 days.

(21) Appl. No.: 17/800,077

(22) PCT Filed: Feb. 17, 2021

(86) PCT No.: PCT/US2021/018298
§ 371 (c)(1),
(2) Date: Aug. 16, 2022

(87) PCT Pub. No.: WO2021/167931
PCT Pub. Date: Aug. 26, 2021

(65) Prior Publication Data
US 2023/0091940 A1     Mar. 23, 2023

Related U.S. Application Data

(60) Provisional application No. 62/977,583, filed on Feb. 17, 2020.

(51) Int. Cl.
*A61B 17/02*      (2006.01)
*A61B 17/00*      (2006.01)

(52) U.S. Cl.
CPC .... *A61B 17/02* (2013.01); *A61B 2017/00477* (2013.01); *A61B 2017/00858* (2013.01)

(58) Field of Classification Search
CPC ................................................. A61B 17/0206
See application file for complete search history.

(56) References Cited

U.S. PATENT DOCUMENTS

| | | | | | |
|---|---|---|---|---|---|
| 3,766,910 | A | * | 10/1973 | Lake | ................... A61B 17/0206 606/198 |
| 3,851,642 | A | * | 12/1974 | McDonald | ............ A61M 29/02 600/223 |
| 6,113,535 | A | * | 9/2000 | Fox | .................... A61B 17/0281 600/201 |
| 6,224,547 | B1 | * | 5/2001 | Doyle | .................... A61B 13/00 600/210 |

(Continued)

*Primary Examiner* — Eduardo C Robert
*Assistant Examiner* — Anna V. Little
(74) *Attorney, Agent, or Firm* — Garrett M. Smith

(57) ABSTRACT

An adaptor configured for use with surgical retractors including a body defining an adaptor surface supporting a plurality of friction grips. The body defines a rear plate opposite the adaptor surface. A mating connecting window is defined in the body. The mating connecting window is configured to receive a surgical retractor head. A connecting element is positioned in the mating connecting window. The connecting element is configured to receive an upper surface of the surgical retractor head. The mating connecting window is configured to conceal the retractor head therein to prevent contact between the retractor head and surgical tissue.

20 Claims, 10 Drawing Sheets

(56)         References Cited

U.S. PATENT DOCUMENTS

| | | | | |
|---|---|---|---|---|
| 6,302,842 | B1 * | 10/2001 | Auerbach | .......... A61B 17/0206 |
| | | | | 600/219 |
| 6,309,349 | B1 * | 10/2001 | Bertolero | ............... A61B 1/313 |
| | | | | 600/210 |
| 2004/0143166 | A1 * | 7/2004 | Larnard | ................. A61B 17/02 |
| | | | | 600/210 |
| 2006/0271096 | A1 * | 11/2006 | Hamada | ............. A61B 17/3439 |
| | | | | 606/198 |
| 2010/0210913 | A1 * | 8/2010 | Sommerich | ........ A61B 17/0293 |
| | | | | 600/203 |
| 2019/0015089 | A1 * | 1/2019 | Rosenbaum | ....... A61B 17/0206 |
| 2019/0059869 | A1 * | 2/2019 | Avalos | ................... A61B 90/11 |
| 2019/0183477 | A1 * | 6/2019 | Damron | ................. A61B 17/02 |

* cited by examiner

ADAPTOR FOR SURGICAL RETRACTORS

FIELD

The present disclosure relates to an adaptor and, more particularly, to an adaptor for surgical retractors.

BACKGROUND

A retractor is a surgical instrument that may be used to separate edges of a surgical incision or wound. Retractors may hold back underlying organs and/or tissues to access underlying body structures. The term retractor generally describes a handheld tool including a curved, hooked, or angled blade and fitted with a handle. When in place, a retractor can maintain a desired position of a given region of tissue. Retractors may be handheld, clamped in place, or supported at an end of a robotic arm. Retractors can also be self-retaining (i.e., not held in place) once inserted by having two or more opposing blades or hooks which are separated, for example, via a spring, ratchet, worm gear or other method. The term retractor is also used to describe distinct, hand-cranked devices such as rib spreaders (also referred to as thoracic retractors, or distractors) with which users may forcefully drive tissues apart to obtain exposure.

SUMMARY

In one aspect of the disclosure, an adaptor configured for use with surgical retractors including a body defining an adaptor surface supporting a plurality of friction grips. The body defines a rear plate opposite the adaptor surface. A mating connecting window is defined in the body. The mating connecting window is configured to receive a surgical retractor head. A connecting element is positioned in the mating connecting window. The connecting element is configured to receive an upper surface of the surgical retractor head. The mating connecting window is configured to conceal the retractor head therein to prevent contact between the retractor head and surgical tissue.

In some aspects of the disclosure, a prong cover is configured to conceal prongs of the surgical retractor head. The prong cover defines an inclined surface extending within the mating connecting window.

In some aspects of the disclosure, the adaptor surface defines an inclined retractor element at an upper surface thereof. The inclined retractor element extends at an angle of from about 1 degree to about 60 degrees with respect to an upper surface of the adaptor surface.

In some aspects of the disclosure, the mating connecting window defines a curved shape at an upper end thereof.

In some aspects of the disclosure, the adaptor and/or the friction grips include or are formed of metal, polymer, rubber, or silicone.

In some aspects of the disclosure, a plurality of stability slots are formed in the adaptor between the friction grips and the mating connecting window.

In some aspects of the disclosure, the friction grips are positioned below the mating connecting window.

Other features of the disclosure will be appreciated from the following description.

BRIEF DESCRIPTION OF THE DRAWINGS

The accompanying drawings, which are incorporated herein and constitute a part of this specification, illustrate aspects and features of the disclosure and, together with the detailed description below, serve to further explain the disclosure, in which.

DETAILED DESCRIPTION

Figure 1:
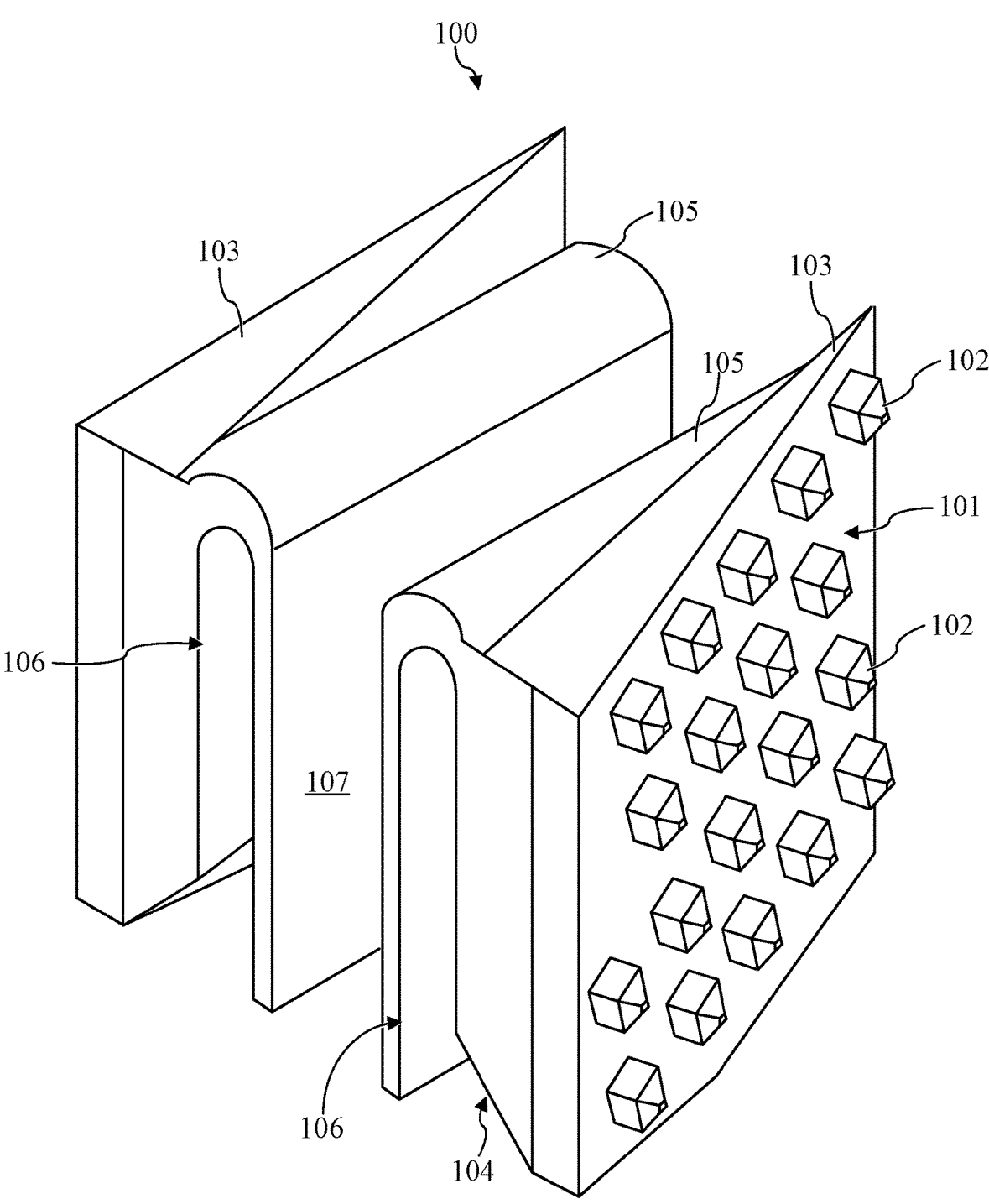
FIG. 1 is a side, perspective view of an adaptor configured for use with surgical retractors in accordance with the aspects and features of present disclosure.
Figure 2:
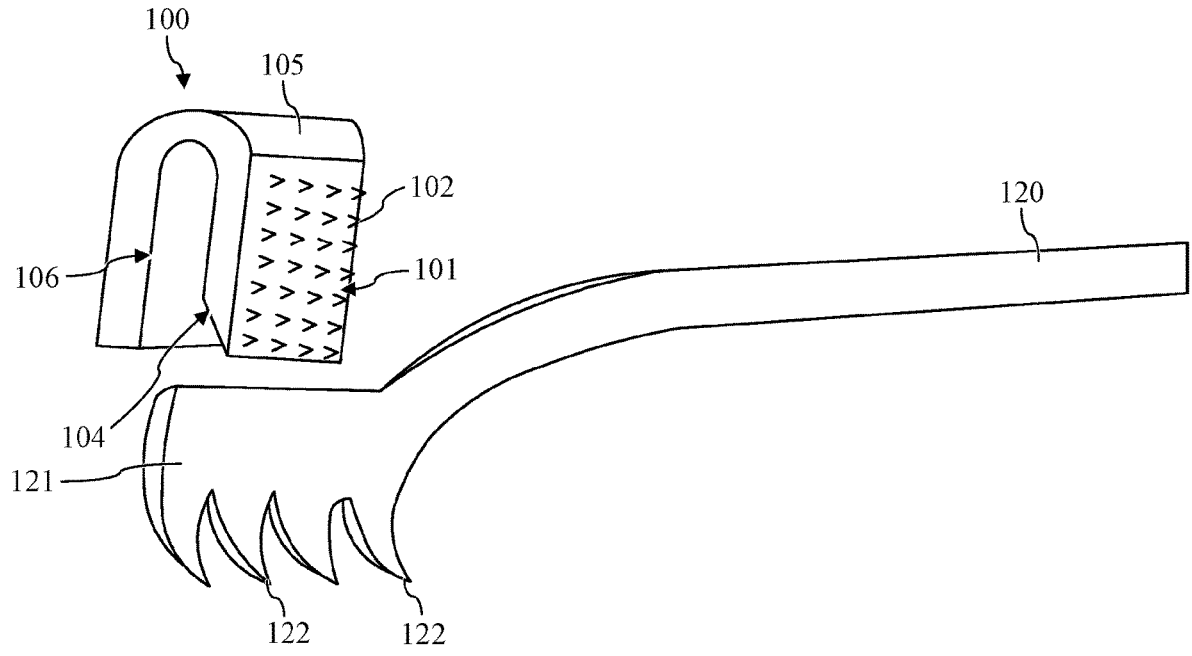
FIG. 2 is a side, perspective view of an exemplary surgical retractor.
Figure 3:
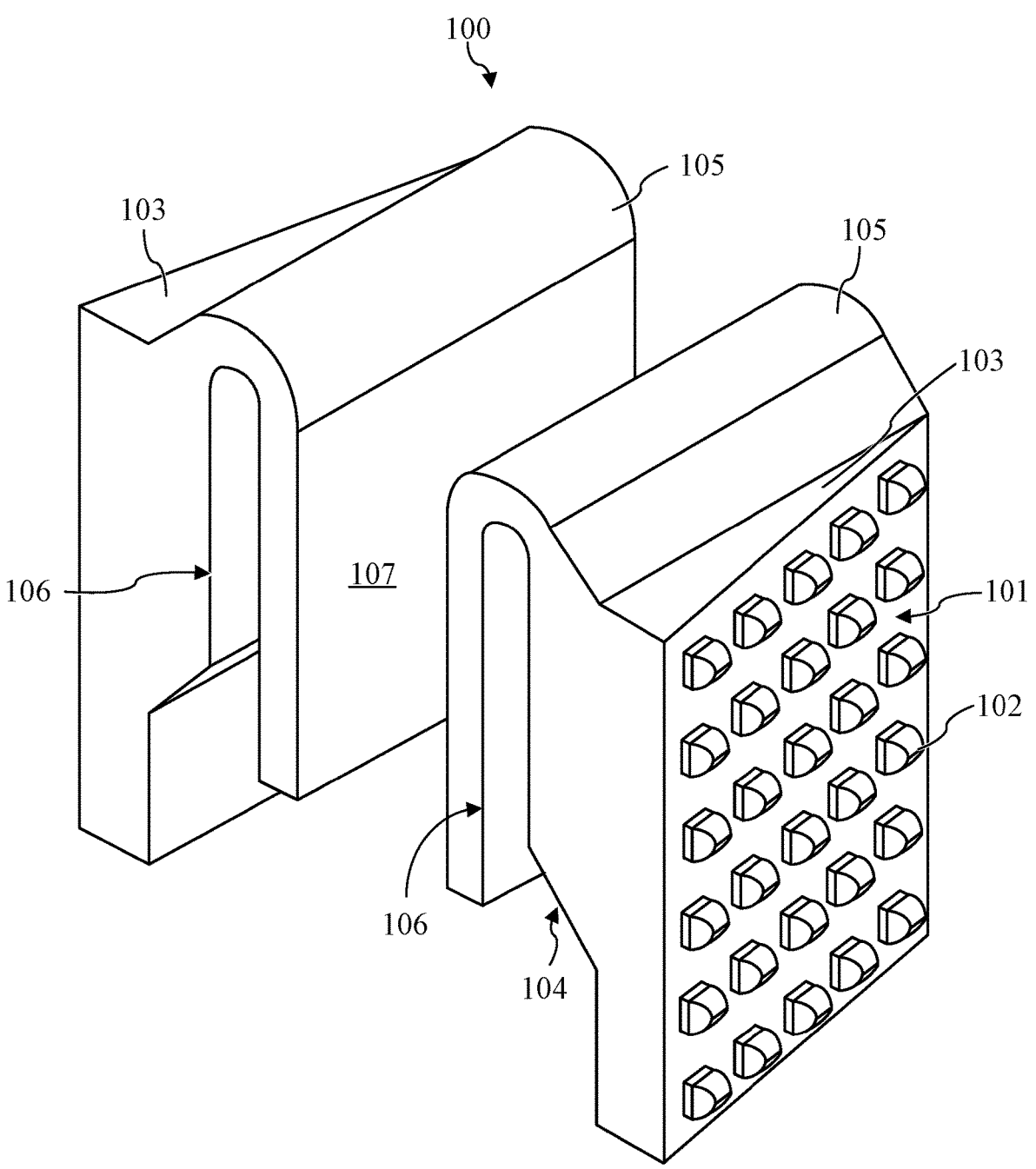
FIG. 3 is a side, perspective view of an adaptor configured for use with surgical retractors in accordance with the aspects and features of present disclosure.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or −10 degrees from true parallel and true perpendicular.

Exemplary axes or directions such as an X-axis direction, a Y-axis direction and a Z-axis direction may be illustrated in the accompanying drawings and/or described herein. As an example, the X-axis direction may perpendicular to the Y-axis direction, and the Z-axis direction may be orthogonal to the X-axis direction and the Y-axis direction.

"About" or "approximately" or "substantially" as used herein may be inclusive of the stated value and means within an acceptable range of variation for the particular value as determined by one of ordinary skill in the art, considering the measurement in question and the error associated with measurement of the particular quantity (e.g., the limitations of the measurement system). For example, "about" may mean within one or more standard variations, or within ±30%, 20%, 10%, 5% of the stated value.

Descriptions of technical features or aspects of an exemplary embodiment of the disclosure should typically be considered as available and applicable to other similar features or aspects in another exemplary embodiment of the disclosure. Accordingly, technical features described herein according to one exemplary embodiment of the disclosure may be applicable to other exemplary embodiments of the disclosure, and thus duplicative descriptions may be omitted herein.

Exemplary embodiments of the disclosure will be described more fully below (e.g., with reference to the accompanying drawings). Like reference numerals may refer to like elements throughout the specification and drawings.

Referring to FIGS. 1-8, retractor system 100 includes adaptor surface 101 which contacts and retracts biological tissue. Adaptor surface 101 may include or may be formed of metal, polymer, rubber, silicone, etc., and can have a flat, curved, square, round, etc., shape, or some combination of shapes and materials thereof. Adaptor surface 101 can have varying length and depth, ranging from approximately 2.25 cm to 6.0 cm for length and approximately 0.5 cm to 6.0 cm for depth or a combination of both thereof, as is clinically relevant.

Figure 4:
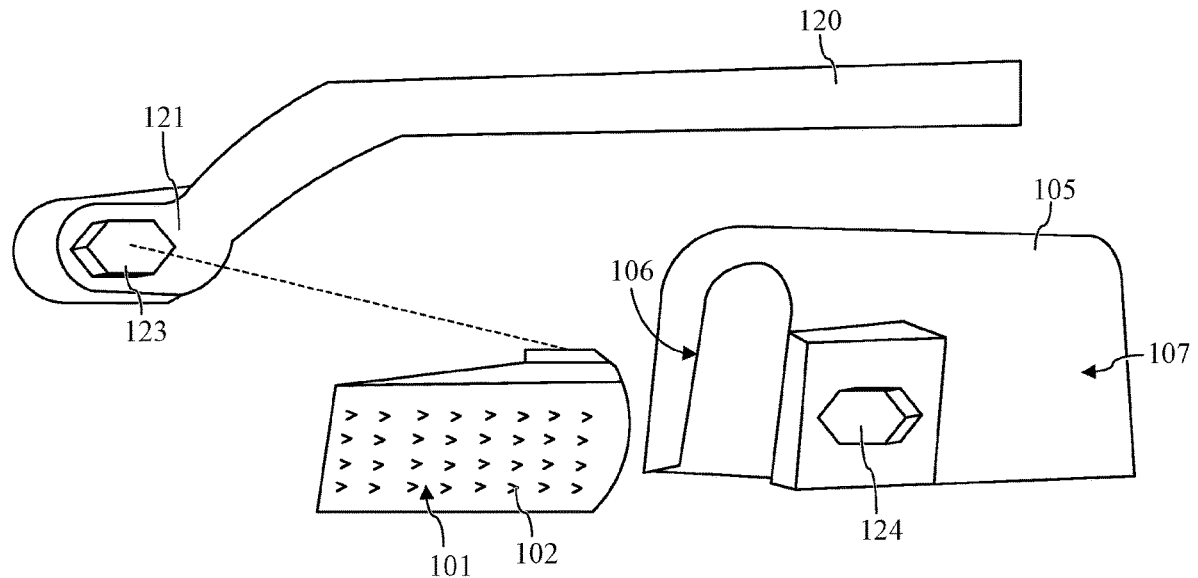
FIG. 4 is a side, perspective view of another exemplary surgical retractor.
Figure 5:
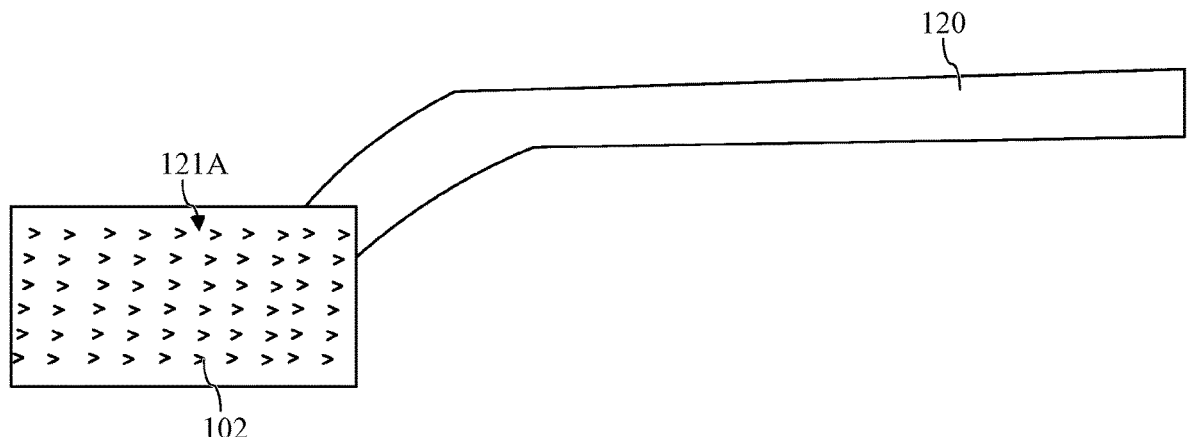
FIG. 5 is a side view of a modified retractor head positioned about a retractor head in accordance with the aspects and features of present disclosure.
Figure 6:
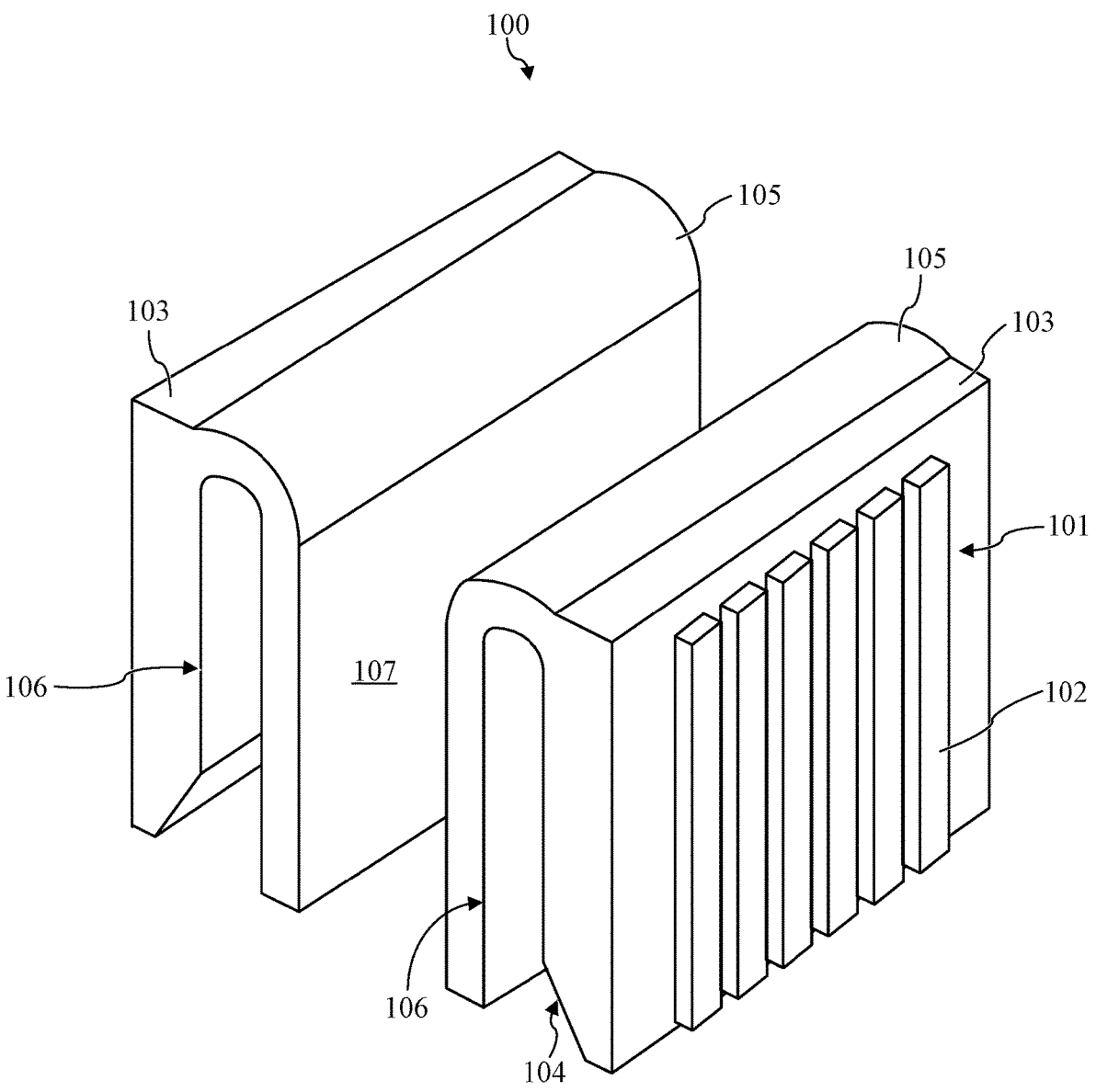
FIG. 6 is a side, perspective view of an adaptor configured for use with surgical retractors in accordance with the aspects and features of present disclosure.

Adaptor surface 101 attaches to retractor head 121 (see, FIG. 2) at the distal end of the retractor by connecting element 105 and mating connecting window 106. Retractor system 100 slips over retractor head 121. Adaptor surface 101, rear plate 107, and prong cover 104 may cover retractor prongs 122 and prevent retractor prongs 122 from contacting patient tissue. Once attached to retractor head 121, adaptor surface 101 does not move unless purposefully removed from retractor head 121. Prong cover 104 may have varying depth, ranging from approximately 2.5 cm to 5 cm, and varying angle from approximately 10 degrees to 40 degrees as per the size of the retractor prongs 122, which may vary. As shown in FIG. 4, retractor system 100 may also attach to retractor head 121 by connecting hole 123 on retractor head 121 and connecting bolt 124 on adaptor surface 101. Connecting bolt 124 may be made of metal, polymer, etc., and may be hexagonal, square, round, circular, etc., or any combination thereof. The shape of connecting hole 123 is empty space and matches the shape of connecting bolt 124. As shown in FIG. 5, retractor system 100 may also comprise a modified retractor head 121A directly attached to retractor arm 120 and has friction grips 102. Modified retractor head 121A contains adaptor surface 101, and all components attached to adaptor surface 101, but is not removable from retractor arm 120 and is permanently attached or manufactured as a unibody.

Adaptor surface 101 may or may not have friction grips 102. Friction grips 102 may be made of metal, polymer, rubber, silicone, etc., and may have a square, rectangular, triangular, round, ellipsoid, ovular, etc., shape, or some combination of shapes and materials thereof. Friction grips 102 may or may not be made of the same material as that of adaptor surface 101. Friction grips 102 may have varying sizes, ranging from approximately 0.25 mm to 2 cm in height and from 0.25 cm to 4 cm in width. Therefore, friction grips 102 may run the entire length/depth of adaptor surface 101 or may only be placed over small areas of adaptor surface 101. Adaptor surface 101 may have varying amounts of friction grips 102, ranging from none to an amount which covers the entirety of adaptor surface 101, and friction grips 102 may be arranged in various patterns on adaptor surface 101 such as linear, scattered, striped, or any pattern, etc.

Figure 7:
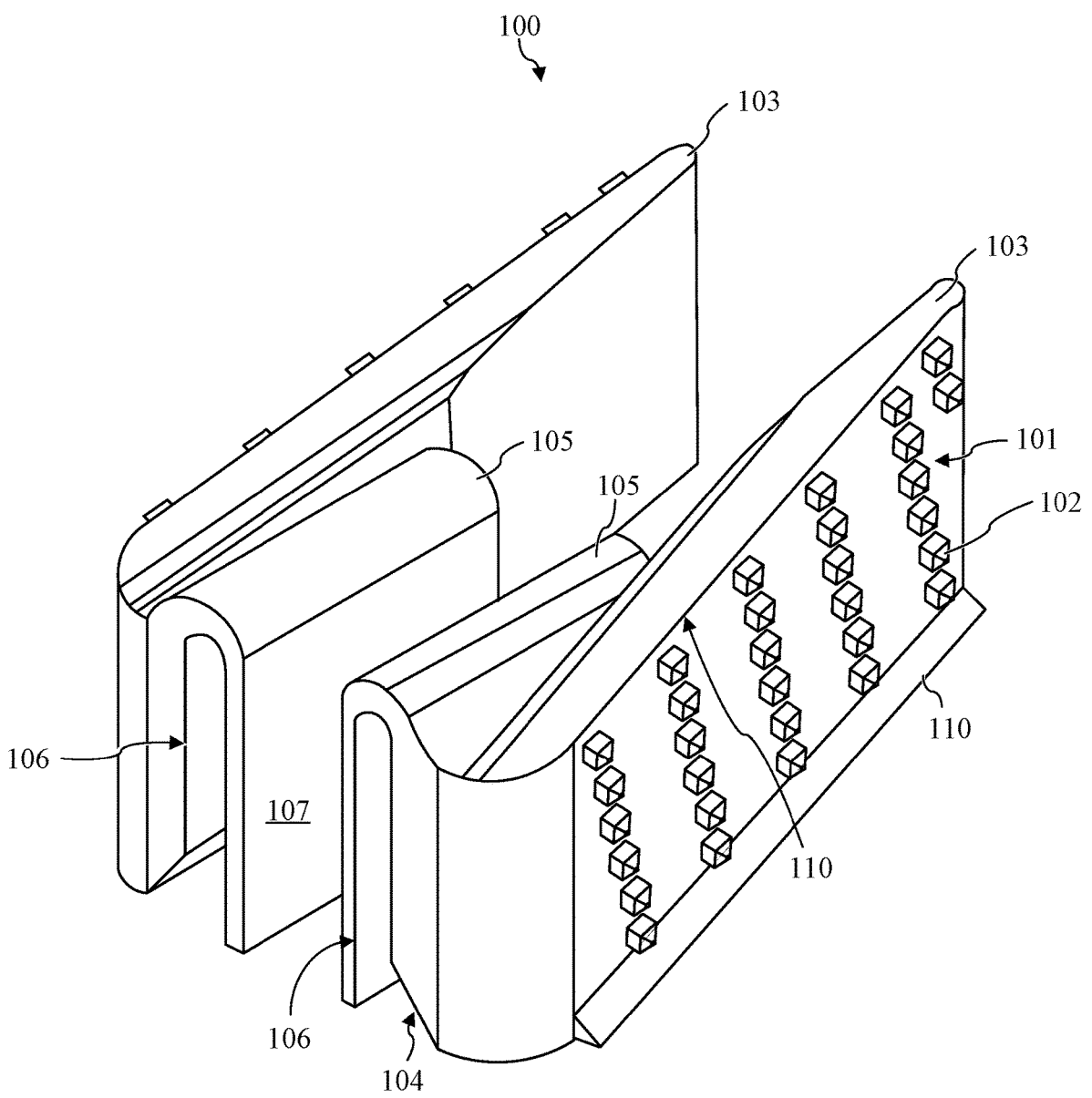
FIG. 7 is a side, perspective view of an adaptor configured for use with surgical retractors in accordance with the aspects and features of present disclosure.
Figure 8:
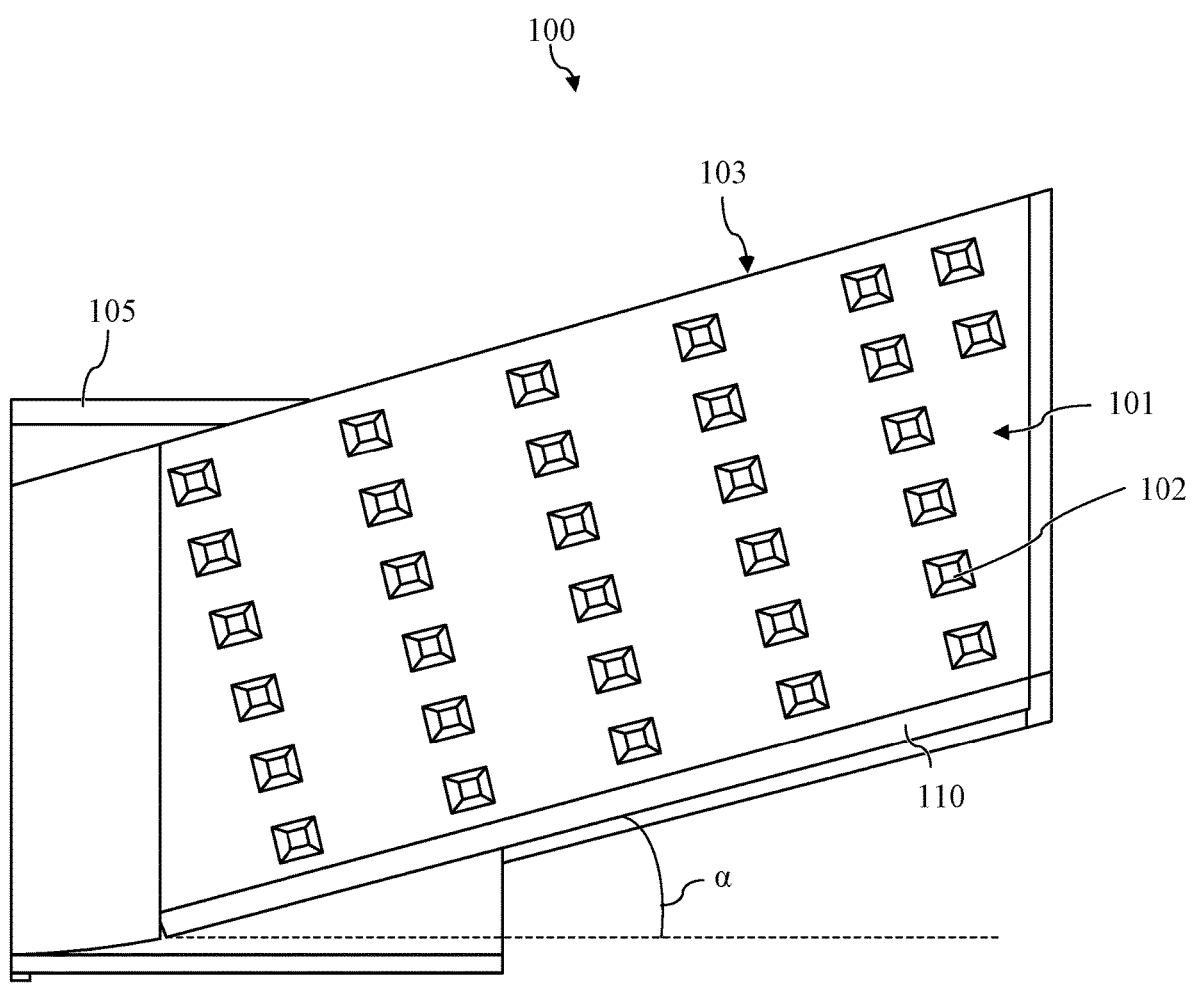
FIG. 8 is an enlarged view of the friction grips of FIG. 7.

In a non-limiting example shown in FIGS. 7 and 8, adaptor surface 101 may have lip 110, which contacts and retracts biological tissue. Lip 110 can have varying size, ranging from approximately 0.25 mm to 1.0 cm, and varying angle with respect to the vertical, ranging from approximately 10 degrees to 45 degrees. Lip 110 may have a flat, round, curved up, etc., shape, as is clinically relevant for retraction. Lip 110 may be made of metal, polymer, rubber, silicone, etc., and may or may not be made of the same material as that of adaptor surface 101.

Adaptor surface 101 may or may not have a corrective angle, which can vary and ranges from approximately −60 degrees to 60 degrees, with respect to the vertical through retractor element 103 (see, FIGS. 7 and 8). Retractor element 103 may or may not be made of the same material as that of adaptor surface 101. Adaptor surface 101 may have varying pitch, ranging from approximately 0 degrees to 45 degrees, with respect to the horizontal (e.g., angle, $\alpha$).

Figure 9:
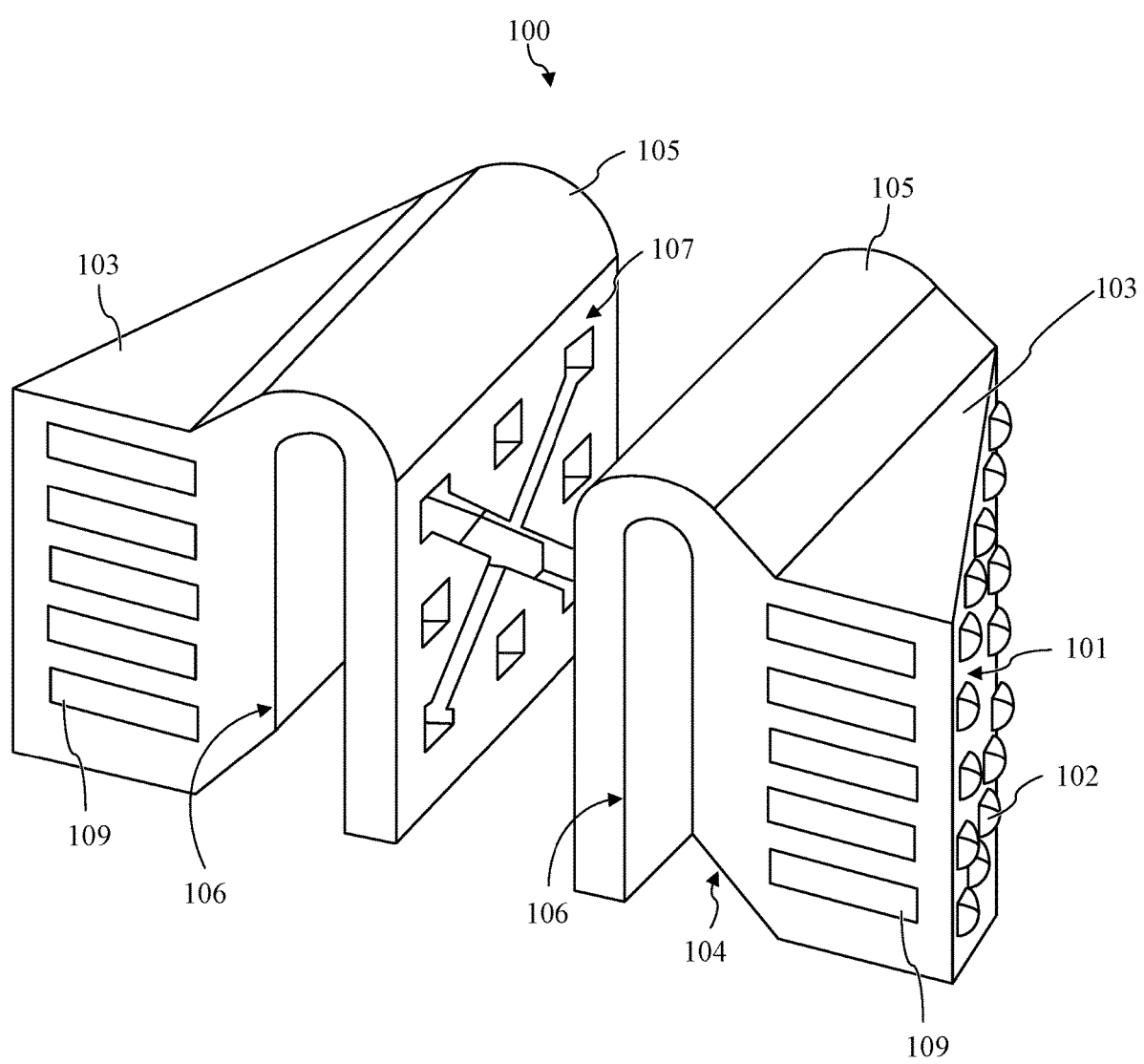
FIG. 9 is a side, perspective view of an adaptor configured for use with surgical retractors in accordance with the aspects and features of present disclosure.

Referring to FIG. 9, the amount of material required for retractor element 103 may be reduced by stability slots 109. Stability slots 109 are empty spaces in retractor elements 103 and may be square, rectangular, circular, ovular, ellipsoid, etc. Stability slots may have varying sizes and volume, as is made possible by the size of retractor elements 103.

Figure 10:
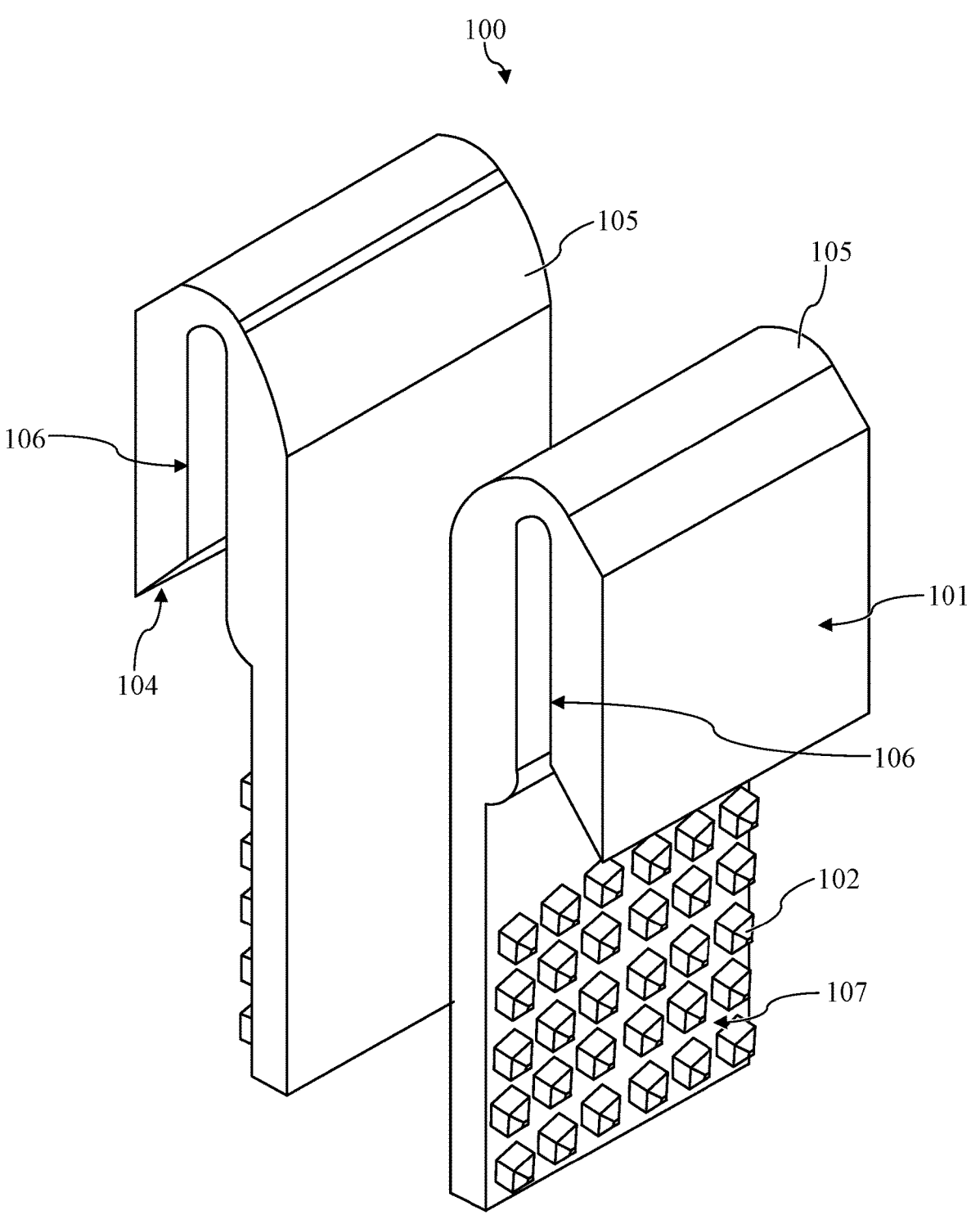
FIG. 10 is a side, perspective view of an adaptor configured for use with surgical retractors in accordance with the aspects and features of present disclosure

FIG. 10 depicts an inverted adaptor surface design, in which friction grips 102 are located on an extended rear plate 107. This extended rear plate 107 comes in contact with biological tissue. retractor system 100 still attaches to retractor head 121 via connecting element 105 and mating connecting window 106.

From the foregoing and with reference to the various figure drawings, those skilled in the art will appreciate that certain modifications can also be made to the disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An adaptor configured for use with surgical retractors, comprising:

a unitary body including:

a rear plate;

a prong cover positioned opposite the rear plate;

a connecting element extending between the rear plate and the prong cover;

a mating connecting window defined by the rear plate, the prong cover, and the connecting element, collectively, the mating connecting window including an opening formed between the rear plate and the prong cover, opposite the connecting element, wherein the mating connecting window configured to receive a surgical retractor head; and an adaptor surface formed adjacent the prong cover and opposite the rear plate, the adaptor surface defining an inclined retractor element at an upper surface thereof; and a plurality of friction grips disposed over and extending from the adaptor surface of the unitary body, the plurality of friction grips made from the same material as the unitary body, wherein the adaptor surface of the unitary body and the plurality of friction grips are configured to contact biological tissue, wherein the connecting element of the unitary body is configured to receive an upper surface of the surgical retractor head, and wherein the mating connecting window of the unitary body is configured to conceal the surgical retractor head therein to prevent contact between the surgical retractor head and the biological tissue.

2. The adaptor of claim 1, wherein the prong cover of the unitary body is configured to conceal prongs of the surgical retractor head.

3. The adaptor of claim 1, wherein the prong cover defines an inclined surface extending within the mating connecting window.

4. The adaptor of claim 1, wherein the inclined retractor element extends at an angle of from about 1 degree to about 60 degrees with respect to an upper surface of the adaptor surface.

5. The adaptor of claim 1, wherein the mating connecting window of the unitary body defines a curved shape at an upper end thereof.

6. The adaptor of claim 1, wherein the unitary body is formed of metal, polymer, rubber, or silicone.

7. The adaptor of claim 1, further including a plurality of stability slots formed in the adaptor between the plurality of friction grips and the mating connecting window.

8. The adaptor of claim 1, wherein each of the plurality of friction grips includes:

a height ranging from approximately 0.25 millimeters (mm) to approximately 2 centimeters (cm), and a width ranging from approximately 0.25 cm to approximately 4 cm.

9. The adaptor of claim 1, wherein the unitary body further includes two lips formed adjacent the adaptor surface, a first lip of the two lips positioned adjacent the connecting element, and a second lip of the two lips positioned adjacent the opening of the mating connecting window.

10. An adaptor configured for use with surgical retractors, comprising:

a body including:

a u-shaped mating connecting window defined by a rear plate, a prong cover, and a connecting element extending between the rear plate and the prong cover, the u-shaped mating connecting window including an opening formed between the rear plate and the prong cover, opposite the connecting element, wherein the mating connecting window is configured to receive a surgical retractor head; and an adaptor surface formed adjacent u-shaped mating connecting window; and a plurality of friction grips disposed over and extending from the adaptor surface of the body, the plurality of friction grips made from the same material as the body, wherein the adaptor surface of the body and the plurality of friction grips are configured to contact biological tissue, wherein the u-shaped mating connecting window of the body is configured to conceal the surgical retractor head therein to prevent contact between the surgical retractor head and biological tissue, and wherein the connecting element of the body defines a curved shape of the u-shaped mating connecting window.

11. The adaptor of claim 10, wherein the prong cover is configured to conceal prongs of the surgical retractor head.

12. The adaptor of claim 10, wherein the prong cover of the body defines an inclined surface extending within the mating connecting window.

13. The adaptor of claim 10, wherein the adaptor surface defines an inclined retractor element at an upper surface thereof.

14. The adaptor of claim 13, wherein the inclined retractor element extends at an angle of from about 1 degree to about 60 degrees with respect to an upper surface of the adaptor surface.

15. The adaptor of claim 10, wherein the body is formed of metal, polymer, rubber, or silicone.

16. An adaptor configured for use with surgical retractors, comprising:

a unitary body including:

a rear plate;

a prong cover positioned opposite the rear plate;

a connecting element extending between the rear plate and the prong cover;

a mating connecting window defined by the rear plate, the prong cover, and the connecting element, collectively, the mating connecting window including an opening formed between the rear plate and the prong cover, opposite the connecting element, wherein the mating connecting window configured to receive a surgical retractor head;

an adaptor surface formed adjacent the prong cover and opposite the rear plate;

a first lip formed adjacent the adaptor surface and positioned adjacent the connecting element; and a second lip formed adjacent the adaptor surface and positioned adjacent the opening of the mating connecting window; and a plurality of friction grips disposed over and extending from the adaptor surface of the unitary body, the plurality of friction grips made from the same material as the unitary body, wherein the adaptor surface of the unitary body and the plurality of friction grips are configured to contact biological tissue, wherein the connecting element of the unitary body is configured to receive an upper surface of the surgical retractor head, and wherein the mating connecting window of the unitary body is configured to conceal the surgical retractor head therein to prevent contact between the surgical retractor head and the biological tissue.

17. The adaptor of claim 16, wherein the prong cover of the unitary body is configured to conceal prongs of the surgical retractor head.

18. The adaptor of claim 16, wherein the prong cover defines an inclined surface extending within the mating connecting window.

19. The adaptor of claim 16, wherein the adaptor surface defines an inclined retractor element at an upper surface thereof.

20. The adaptor of claim 16, wherein the mating connecting window of the unitary body defines a curved shape at an upper end thereof.

* * * * *